United States Patent
Park et al.

(10) Patent No.: US 9,447,383 B2
(45) Date of Patent: Sep. 20, 2016

(54) MDCK-DERIVED CELL LINES ADAPTED TO SERUM-FREE CULTURE AND SUSPENSION CULTURE AND METHOD FOR PREPARING VACCINE VIRUS USING THE CELLS

(71) Applicant: SK Chemicals Co., Ltd., Suwon, Gyeonggi-Do (KR)

(72) Inventors: Yong Wook Park, Gyeonggi-Do (KR); Kun Se Lee, Seoul (KR); Bong-Yong Lee, Seoul (KR); Mahnhoon Park, Gyeonggi-Do (KR); Hun Kim, Gyeonggi-Do (KR); Yun-Hee Kim, Gyeonggi-Do (KR); Su-Jeen Lee, Gyeongg-Do (KR)

(73) Assignee: SK Chemicals Co., Ltd., Suwon, Gyeonggi-do (KR)

(*) Notice: Subject to any disclaimer, the term of this patent is extended or adjusted under 35 U.S.C. 154(b) by 0 days.

(21) Appl. No.: 14/711,489

(22) Filed: May 13, 2015

(65) Prior Publication Data

US 2015/0247128 A1     Sep. 3, 2015

Related U.S. Application Data

(63) Continuation of application No. 13/785,757, filed on Mar. 5, 2013, now abandoned, which is a continuation of application No. PCT/KR2011/006589, filed on Sep. 6, 2011.

(30) Foreign Application Priority Data

Aug. 26, 2011 (KR) .......................... 10-2011-0085902

(51) Int. Cl.
*C12N 7/00*     (2006.01)
*A61K 39/145*   (2006.01)
*A61K 39/12*    (2006.01)
*C12N 5/071*    (2010.01)
*A61K 39/00*    (2006.01)

(52) U.S. Cl.
CPC ................ *C12N 7/00* (2013.01); *A61K 39/12* (2013.01); *A61K 39/145* (2013.01); *C12N 5/0686* (2013.01); *A61K 39/00* (2013.01); *A61K 2039/525* (2013.01); *A61K 2039/5254* (2013.01); *C12N 2500/90* (2013.01); *C12N 2760/16134* (2013.01); *C12N 2760/16151* (2013.01); *C12N 2760/16152* (2013.01); *C12N 2760/16171* (2013.01); *C12N 2760/16234* (2013.01); *C12N 2760/16251* (2013.01); *C12N 2760/16252* (2013.01); *C12N 2760/16271* (2013.01)

(58) Field of Classification Search
None
See application file for complete search history.

(56) References Cited

U.S. PATENT DOCUMENTS 6,825,036 B2    11/2004  Makizumi et al.
2006/0188977 A1  8/2006  Schwartz et al.

FOREIGN PATENT DOCUMENTS

DE      10144906 A1       3/2003
WO      WO-2008032219 A2  3/2008
WO      WO-2010036760 A1  4/2010

*Primary Examiner* — Janet L Andres
*Assistant Examiner* — Nick Zou
(74) *Attorney, Agent, or Firm* — Mintz Levin Cohn Ferris Glovsky and Popeo, P.C.; Kongsik Kim

(57) ABSTRACT

Disclosed is a Madin-Darby canine kidney (MDCK)-derived cell line. The MDCK-derived cell line is derived from MDCK cells deposited under accession number ATCC CCL-34. The MDCK-derived cell line can be prepared by serum-free culture and suspension culture. Preferably, the MDCK-derived cell line has low or no tumorigenicity. The MDCK-derived cell line is preferably selected from MDCK Sky1023, MDCK Sky10234 and MDCK Sky3851. Further disclosed are a culture method for growing the MDCK-derived cells and a method for producing a vaccine virus using the MDCK-derived cells.

1 Claim, 3 Drawing Sheets

MDCK-DERIVED CELL LINES ADAPTED TO SERUM-FREE CULTURE AND SUSPENSION CULTURE AND METHOD FOR PREPARING VACCINE VIRUS USING THE CELLS

CROSS-REFERENCE TO RELATED APPLICATIONS

This application is a continuation of U.S. patent application Ser. No. 13/785,757, filed Mar. 5, 2013, which is a continuation under 35 U.S.C. § 119(a) of PCT Patent Application No. PCT/KR2011/006589 filed on Sep. 6, 2011, which claims priority to PCT/KR2010/006041, filed on Sep. 6, 2010, and Korean Patent Application No. 10-2011-0085902, filed in the Republic of Korea on Aug. 26, 2011, the entire contents of which are incorporated herein by reference.

TECHNICAL FIELD

The present invention relates to a novel MDCK-derived cell line that can be prepared by serum-free culture and suspension culture without the need to be attached to carriers, a method for preparing the MDCK-derived cell line, and a method for producing a vaccine virus using the MDCK-derived cell line.

BACKGROUND

Fertilized eggs, mouse brains, primary cells and established cells are generally used as sources for the production of vaccines. However, such traditional vaccine sources have several problems. For example, when it is intended to use fertilized chicken eggs for vaccine production, there are difficulties in raising chickens, managing the fertilized eggs depending on vaccine production schedules and purifying ingredients derived from egg proteins.

Fetal calf serum is generally added as a growth factor for cell culture. However, serum is susceptible to contamination with prions and viruses and its commercial products might vary in quality. Moreover, high-quality fetal calf serum products derived from Australian and New Zealand calves are highly priced, resulting in an increase in production cost.

MDCK cell lines are established cell lines where various kinds of viruses can proliferate. Since MDCK cell lines exhibit a strong tendency to attach to other surfaces, large-area culture vessels and carriers are required for large-scale culture, incurring considerable costs. Specifically, investment costs for culture equipment or carriers are vast and a processing step is needed to remove cells attached to carriers, posing the risk of loss of and damage to the cells. Thus, there is a need for a cell line that can be prepared by serum-free culture and suspension culture and is thus suitable for use in the production of a vaccine through animal cell culture in an economical and safe manner.

U.S. Pat. No. 6,825,036 discloses an MDCK-derived cell line that can be grown in serum-free culture and in suspension culture without a solid carrier. The U.S. Patent employs two approaches for the adaptation of the cell line to suspension culture. According to the first approach, the MDCK-derived cell line is obtained by direct suspension culture in a spinner flask. In this case, the cell density does not reach $1.0 \times 10^6$ cells/ml, a level necessary for industrial-scale production. According to the second approach, the MDCK-derived cell line is obtained by culturing the original MDCK cells in the presence of beads as carriers, expanding the culture scale and growing the cultured cells in the absence of carriers. The second approach has the disadvantage in that the procedure is relatively complicated.

There are several reports that original MDCK cell lines are tumorigenic. Thus, there exists a danger of potential tumorigenicity when original MDCK cell lines are used for vaccine production. Under these circumstances, there is a need to develop a novel cell line that can be prepared by serum-free culture and suspension culture and preferably has very low tumorigenicity or is non-tumorigenic.

SUMMARY

The present invention is designed to solve the problems of the prior art, and therefore it is an object of the present invention to provide an MDCK-derived cell line that can be advantageously prepared by serum-free culture and suspension culture and has very low or no tumorigenicity as compared to original MDCK cell lines that can be used to grow vaccine viruses. It is another object of the present invention to provide a method for producing a virus, particularly an influenza virus, using the cell line.

In order to achieve the above objects, the present invention provides a particular Madin-Darby canine kidney (MDCK)-derived cell line that is derived from MDCK cells deposited under accession number ATCC CCL-34, does not require serum for cell growth and can be prepared by suspension culture without the need to be attached to carriers.

The MDCK-derived cell line of the present invention can be prepared through the following steps: S1) adapting an original MDCK cell line to a serum-free medium to prepare a cell line adapted to the serum-free culture; and S2) directly adapting the cell line adapted to the serum-free culture to suspension culture without undergoing carrier adaptation and screening the desired cell line.

More specifically, the MDCK-derived cell line of the present invention can be prepared by a method including (a) preparing original MDCK cells deposited under accession number ATCC CCL-34, (b) adapting the original MDCK cells to a chemically defined serum-free medium to allow the original MDCK cells to grow in the serum-free medium, and (c) inducing direct adaptation of the adherent MDCK cells adapted in step (b) to suspension culture in a chemically defined serum-free medium without undergoing carrier adaptation to allow the MDCK cells to grow in a suspension state without carriers.

The MDCK-derived cell line newly established by the method can be prepared by serum-free culture and suspension culture. The MDCK-derived cell line of the present invention is preferably selected from MDCK Sky1023 (DSM ACC3112), MDCK Sky10234 (DSM ACC3114) and MDCK Sky3851 (DSM ACC3113), which have been deposited at the Deutsche Sammlung von Mikroorganismen and Zellkulturen (DSMZ), Braunschweig, Germany, on Jan. 27, 2011.

The term "serum-free medium" as used herein means a medium to which serum is not substantially added and in which the established cell line of the present invention can be prepared by culture.

The expression "serum is not substantially added" means that serum is present in an amount of 0.5 vol % less, preferably 0.1 vol % or less, more preferably 0.01 vol % or less, most preferably not present at all.

U.S. Pat. No. 6,825,036 employs two approaches to prepare an MDCK-derived cell line in a serum-free medium by suspension culture. The first approach tries direct suspension culture of an original MDCK cell line in a spinner flask. In this case, the cell density does not reach $1.0 \times 10^6$ cells/ml, a level necessary for industrial-scale production. According to the second approach, the MDCK-derived cell line is obtained by culturing the original MDCK cells in the presence of carriers and growing the cultured cells in the absence of carriers.

In contrast, the present invention tries direct culture of original MDCK cells in a spinner flask without undergoing carrier adaptation to prepare a newly established cell line that can be prepared in a serum-free medium by suspension culture. The established cell line B-702 of U.S. Pat. No. 6,825,036 reaches a cell density of $1.0 \times 10^6$ cells/ml within a week, whereas the established cell line of the present invention reaches a cell density of at least $1.0 \times 10^6$ cells/ml within about 3 days, indicating much superior proliferation potential.

Several reports state that previously known MDCK cell lines are tumorigenic. In contrast, the established cell line of the present invention has very low or no tumorigenicity when compared to the known MDCK cell lines. Specifically, the newly established MDCK-derived cell lines prepared in the Examples section were confirmed to have very low or no tumorigenicity when compared to existing MDCK cell lines through tests using the cell lines, cell lysates and cell DNAs in nude mice. From these test results, it can be concluded that the MDCK-derived cell line of the present invention is stable enough to be used for vaccine production. More preferably the MDCK-derived cell line of the present invention can be prepared by serum-free culture and suspension culture.

The present invention also provides a method for producing a vaccine virus using the MDCK-derived cell line. Examples of viruses that can be grown using the MDCK-derived cell line include influenza viruses, measles viruses, Japanese encephalitis viruses, mumps viruses, rubella viruses, polio viruses, HSV-1, HSV-2, rabies viruses, RS viruses, reovirus type 3, yellow fever virus, parvoviruses, coxsackie viruses, adenovirus types 1 to 47, Lassa viruses and vacciniaviruses. The MDCK-derived cell line of the present invention is most suitable for use in the production of influenza viruses.

More specifically, the present invention provides a method for producing an influenza virus from a cell culture, the method including: (a) inoculating a serum-free culture medium with the MDCK-derived cells at a concentration of about $1 \times 10^4$ to about $1 \times 10^6$ cells/ml; (b) allowing the MDCK-derived cells to grow in a disposable bioreactor system until the cell density reaches at least about $5 \times 10^6$ cells/ml, including culturing the MDCK-derived cells while maintaining one or more culture conditions selected from the group consisting of a stirring rate of about 40 to about 100 rpm, a pH of about 6.5 to about 7.5 and a dissolved oxygen (DO) concentration of about 35 to about 100%; (c) infecting the grown MDCK-derived cells with an influenza virus; (d) culturing the infected grown MDCK-derived cells under conditions allowing cloning of the influenza virus; and (e) isolating the influenza virus from the cell culture composition. Preferably, the influenza virus production method of the present invention further includes adding a fresh medium to the cell culture or replacing a portion of the medium with a fresh medium in step (b).

The present invention also provides a virus or a virus antigen produced by the virus production method. The present invention also provides an immunogenic pharmaceutical composition including the virus antigen.

The novel MDCK-derived cell line of the present invention can be prepared by serum-free culture and suspension culture and has the advantage of very low or no tumorigenicity. In addition, the novel MDCK-derived cell line of the present invention can be efficiently used for virus proliferation. Furthermore, the novel MDCK-derived cell line of the present invention is suitable for use in the production of a virus, particularly an influenza virus.

BRIEF DESCRIPTION OF THE DRAWINGS

The accompanying drawings illustrate preferred embodiments of the invention and, together with the foregoing disclosure, serve to provide further understanding of the technical spirit of the invention. However, the present invention is not to be construed as being limited to the drawings.

DETAILED DESCRIPTION

Figure 1:
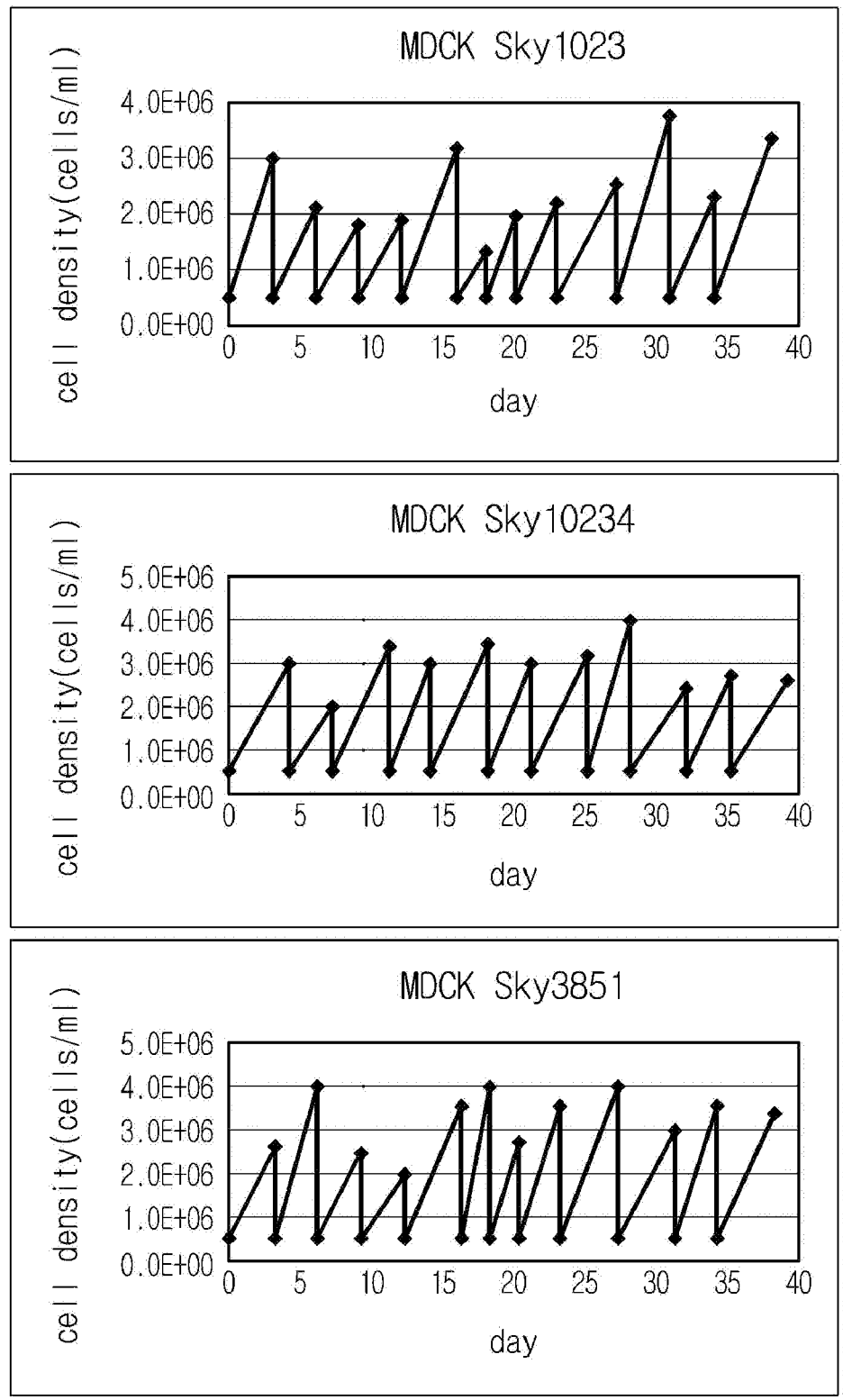
FIG. 1 shows cell growth profiles of MDCK-derived cell lines during suspension culture in spinner flasks.

The following examples are provided to assist in a further understanding of the invention. However, these examples may take several other forms, and the scope of the invention should not be construed as being limited thereto. These examples are provided to more fully explain the invention to those having ordinary knowledge in the art to which the invention belongs.

Example 1

Preparation of MDCK-derived Cell Lines by Serum-free Culture and Suspension Culture CCL-34, an MDCK cell line, was furnished from ATCC. CCL-34 was cultured in an EMEM medium supplemented with 10% serum in a T-25 flask at 37° C. and 5% $CO_2$. After the cells were expanded, they were cultured in a medium consisting of the EMEM medium and a serum-free medium (50%). It was confirmed whether growth of the cells was normal or not during culture. When growth of the cells was confirmed to be normal, the grown cells were cultured in a medium containing a serum-free medium (75%). This procedure was repeated to obtain a cell line adapted to a serum-free medium (100%). EX-CELL MDCK (Sigma), UltraMDCK (Lonza) and VP-SFM (Invitrogen) may be used as the media for serum-free culture.

The cell line adapted to the serum-free medium was sufficiently expanded in a T-flask. Thereafter, the expanded cell line was adapted to suspension culture with stirring at a rate of 40-80 rpm in a spinner flask (Corning) at 37° C. and 5% $CO_2$. When the pH of the culture medium was decreased or the cells were grown above a predetermined level, the medium was exchanged with a new one or the cells were subcultured. After adaptation to suspension culture for 3-6 months, the cell concentration reached $2 \times 10^6$ cells/ml or more. The cell viability was 95% or above and suspension culture into single cells was observed. EX-CELL 302 CHO (Sigma), UltraCHO (Lonza) and SMIF-6 (Invitrogen) may be used as the media for suspension culture. As a result of the serum-free culture and suspension culture, three kinds of MDCK-derived cell lines were obtained and termed MDCK Sky1023, MDCK Sky10234 and MDCK Sky3851.

Example 2

Evaluation of Proliferation Potentials of the Cell Lines

The MDCK-derived cell lines prepared by culture in the serum-free media were cultured under the conditions indicated in Table 1. The proliferation potentials of the MDCK-derived cell lines were evaluated. The MDCK cell line (ATCC CCL-34) as a control was grown in a medium supplemented with 10% serum.

TABLE 1

|  | MDCK-derived cell lines | Control (ATCC CCL-34) |
|---|---|---|
| Culture media | EX-CELL MDCK (Sigma), UltraMDCK (Lonza), VP-SFM (Invitrogen) | EMEM (Lonza) |
| Additives | L-Glutamine (Lonza) 2% v/v | L-Glutamine (Lonza) 2% v/v, Fetal calf serum (Lonza) 10% v/v |
| Culture conditions | 37° C., 5% $CO_2$, moist | 37° C., 5% $CO_2$, moist |
| Culture volume | T-75 flask (15 ml) | T-75 flask (15 ml) |

The cell concentrations were about $1.0 \times 10^5$ cells/ml at the beginning of culture. When the cell concentrations reached about $1 \times 10^6$ cells/ml or 3-4 days after the culture, the cells were subcultured. The cell concentrations at the beginning of subculture were adjusted to $1 \times 10^5$ cells/ml.

Each of the MDCK-derived cell lines grown in the serum-free media showed a cell growth rate comparable to that of the MDCK cell line grown in the serum medium.

Example 3

Evaluation of Proliferation Profiles and Subculture Stability of the Cell Lines After the three kinds of cell lines adapted to serum-free culture and suspension culture were continuously cultured in respective spinner flasks, their proliferation profiles and subculture stability were evaluated. The cell concentrations at the beginning of culture were adjusted to about $4 \times 10^5$ cells/ml. About 3-4 days after the culture, the cell concentrations reached about $2 \times 10^6$ cells/ml or more. The culture was conducted under the following conditions. The results are shown in FIG. 1.

Initial cell concentration: $4 \times 10^5$ cells/ml
Culture scale: 50 ml spinner flask
Spinner rotational rate: 60 rpm
Culture conditions: 37 ° C., 5% $CO_2$, moist
Subculture condition: 3-4 days after culture

Example 4

Evaluation of Virus Proliferation

2010/2011 seasonal influenza vaccine strains were grown using the MDCK-derived cells under the following suspension culture conditions:

Cell concentration: $2 \times 10^6$ cells/ml
Culture scale: 1,000 ml spinner flask
Spinner rotational speed: 60 rpm
Culture conditions: 34 ° C., 5% $CO_2$, moist
Culture period: 3 days It is commonly known that influenza viruses are better grown during culture at 34° C. than at 37° C., which was experimentally confirmed. Trypsin was included in culture media to infect the cell lines with the influenza viruses during culture. The titers of the influenza viruses were measured by haemagglutination assay. After culture for 3 days, most of the cells were killed. The culture supernatants were collected and the titers of the viruses were measured. The results are shown in Table 2. As can be seen from the results in Table 2, most of the viruses showed HA titers of 1024 or more. The growth levels of the viruses were similar to those of eggs or MDCK cells cultured in 10% FBS containing media. These results have proved that the MDCK-derived cell lines are suitable for efficient production of viruses under serum-free culture and suspension culture conditions.

TABLE 2

| Virus | MDCK Sky1023 | MDCK Sky10234 | MDCK Sky3851 |
|---|---|---|---|
| A/California/07/2009 (H1N1) | 512 | 1024 | 2048 |
| A/perth/16/2009 (H3N2) | 1024 | 1024 | 4096 |
| B/Brisbane/60/2008 | 4096 | 2048 | 4096 |

Example 5

Identification of the Ability of the Grown Viruses to Form Antibodies

Figure 2:
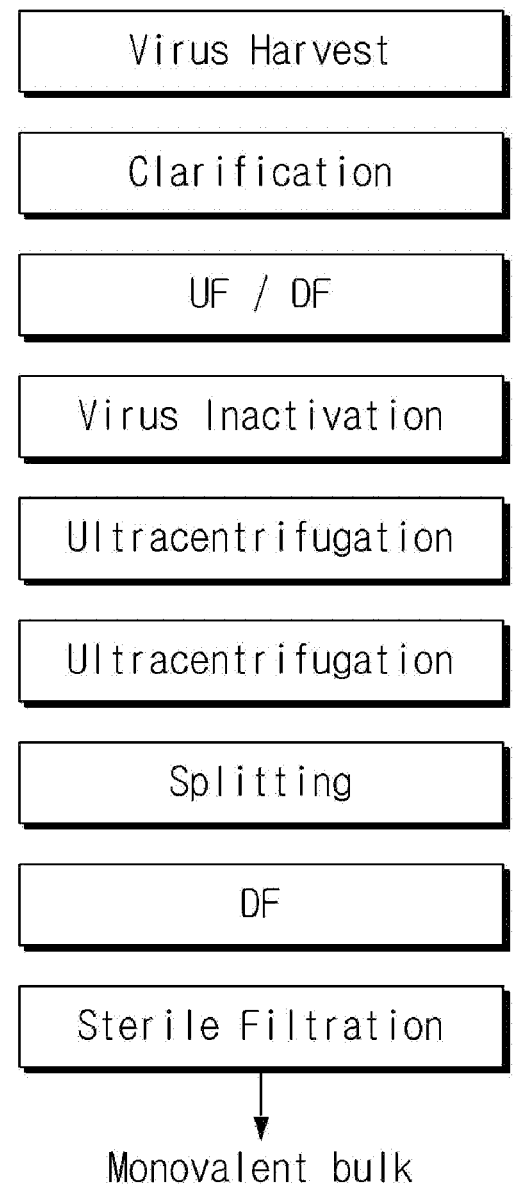
FIG. 2 is a flow chart showing a representative purification process of an influenza virus.
Figure 3:
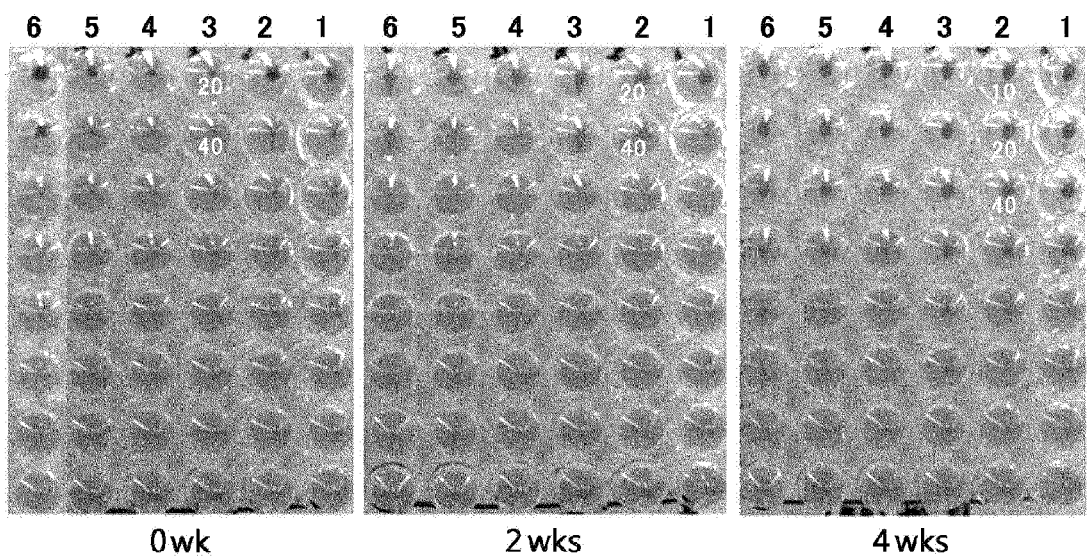
FIG. 3 shows HI serum test results obtained in animal experiments using purified samples of viruses grown in MDCK-derived cell lines.

To identify the ability of the influenza viruses grown in the MDCK-derived cells to form antibodies, the viruses were purified from the culture solutions and inoculated into mice. The antibody values of the viruses were measured. A flow chart of the purification process is shown in FIG. 2, and a brief explanation thereof is given below.

First, each of the virus culture solutions was centrifuged to remove cell lysates therefrom and filtered through a 0.45 μm filter. The filtrate was concentrated by ultrafiltration using a 300 kDa cut-off cartridge, and the virus was inactivated with formalin. Thereafter, the virus was isolated from the culture solution by ultracentrifugation through a sucrose concentration gradient. The virus was disrupted by treatment with Triton X-100, concentrated by ultrafiltration to remove the detergent, filtered through a 0.2 μm filter to sterilize, affording a vaccine solution.

The purified solutions of the virus strain A/California/07/2009 (H1N1) grown using the three MDCK-derived cell lines MDCK Sky1023, MDCK Sky10234 and MDCK Sky3851 were used for animal experiments to identify the efficacy of the virus strain. As a control, a 08/09 seasonal influenza vaccine (IVR-148, NYMC X-175C, B/Florida/4/2006) was used. A total of six test groups were used, each of which was inoculated into five mice. Serum samples from the five mice were collected. A haemagglutination inhibition (HI) test was conducted on the collected serum to measure the antibody value of the virus.

Serum was obtained by drawing blood from the retro-orbital plexus of the mice using a capillary tube prior to injection (0 week) of the test group into the mice. After the blood drawing, a total of 200 μl of the test group was injected into the hind legs (100 μl for each leg) of each of the mice via the IM route. Two weeks after the injection, serum was obtained by drawing blood from the retro-orbital plexus in the same manner as above. The same amount of the test group as that injected at 0 week was inoculated into each of the mice to boost the ability to form antibodies. Four weeks after the injection, serum was obtained by drawing blood from the retro-orbital plexus in the same manner as above.

The obtained serum samples were treated by the following procedure. The serum samples drawn from the mice were collected and divided into 30 µl samples. 90 µl of RDE was added to each 30 µl sample and was allowed to stand at 37° C. for at least 18 hr. The mixture was further left standing at 56° C. for at least 30 min to inactivate the RDE. Subsequently, 120 µl of 0.85% physiological saline and 15 µl (a volume corresponding to 1/20 of the total volume) of chicken red blood cells were subsequently added, sufficiently suspended, and left standing at 4° C. for 1 hr. The settled blood cells were re-suspended at 30-min intervals. Thereafter, the suspension was centrifuged at 1,200 rpm for 10 min to separate the serum. HI test was conducted on the serum to measure the antibody value of the serum. The measured results are shown in Table 3. All experimental groups were measured to have HI titers of 40 or more. That is, when the virus cultured from the MDCK-derived cells was injected into the animals, similarly to the existing vaccine, it was confirmed that antibodies against the virus were formed. From these results, it can be concluded that the MDCK-derived cell lines are useful for the production of virus vaccines.

TABLE 3

| Experimental group | Cell line | Amount of antigen inoculated | HI titer |
| --- | --- | --- | --- |
| 1 | MDCK Sky1023 | 15 µg/mouse | 80 |
| 2 | MDCK Sky10234 | 15 µg/mouse | 160 |
| 3 | MDCK Sky10234 | 7.5 µg/mouse | 160 |
| 4 | MDCK Sky3851 | 15 µg/mouse | 80 |
| 5 | MDCK Sky3851 | 7.5 µg/mouse | 80 |
| 6 | Reference vaccine | | 320 |

Example 6

Identification of Tumorigenicity of the Cell Lines in Nude Mice

To evaluate the tumorigenicity of the cell lines MDCK Sky1203 and MDCK Sky3851, the MDCK-derived cell lines and substances derived therefrom (including cell lysates and cell DNAs) were transplanted into the hypodermis of BALB/c-nu/nu mice as test animals, as indicated in Table 4. An observation was made to determine whether tumors were formed for 12 weeks. The cells were inoculated in doses of $10^1$, $10^3$, $10^5$ and $10^7$ cells, the cell lysates were inoculated in doses of $10^5$ and $10^7$ cells, and the cell DNAs were inoculated in doses of $10^5$ and $10^7$ cells. Each of the groups was inoculated into 5-10 mice. The experimental results are shown in Table 4. The cell lines MDCK Sky1023 and MDCK Sky3851 were confirmed to have low or no tumorigenicity when compared to the original MDCK (ATCC) cell line as an internal control.

TABLE 4

| Experimental group | Experimental sample | Dose | Number of animals where tumor was found |
| --- | --- | --- | --- |
| Negative control | PBS | | 0/5 |
| Positive controls | HeLa Cells | $10^5$ | 1/5 |
| | HeLa Cells | $10^7$ | 5/5 |
| Internal groups | MDCK | $10^1$ | 0/10 |
| | MDCK | $10^3$ | 0/10 |
| | MDCK | $10^5$ | 10/10 |
| | MDCK | $10^7$ | 9/10 |
| MDCK Sky1023 | Cells | $10^1$ | 0/10 |
| | | $10^3$ | 0/10 |
| | | $10^5$ | 3/10 |
| | | $10^7$ | 10/10 |
| | Cell lysates | $10^5$ | 0/5 |
| | | $10^7$ | 0/5 |
| | DNAs | $10^5$ | 0/5 |
| | | $10^7$ | 0/5 |
| MDCK Sky3851 | Cells | $10^1$ | 0/10 |
| | | $10^3$ | 0/10 |
| | | $10^5$ | 0/10 |
| | | $10^7$ | 0/10 |
| | Cell lysates | $10^5$ | 0/5 |
| | | $10^7$ | 0/5 |
| | DNAs | $10^5$ | 0/5 |
| | | $10^7$ | 0/5 |

Accession Number

The name of the depositary authority: DEUTSCHE SAMMLUNG VON MIKROOGANISMEN UND ZELLKULTUREN GmbH The accession number: DSMACC3112

The date of the deposit: 20110127

The name of the depositary authority: DEUTSCHE SAMMLUNG VON MIKROORGANISMEN UND ZELLKULTUREN GmbH The accession number: DSMACC3113

The date of the deposit: 20110127

The name of the depositary authority: DEUTSCHE SAMMLUNG VON MIKROORGANISMEN UND ZELLKULTUREN GmbH The accession number: DSMACC3114

The date of the deposit: 20110127

What is claimed:

1. A MDCK-derived cell line which is MDCK Sky1023 (DSM ACC3112), MDCK Sky10234 (DSM ACC3114) or MDCK Sky3851 (DSM ACC3113).

* * * * *